United States Patent [19]
Frank et al.

[11] B 3,987,098
[45] Oct. 19, 1976

[54] QUATERNARY ARYLAMINOALKYL PHOSPHONIUM SALTS

[75] Inventors: Arlen W. Frank, Slidell; George L. Drake, Jr., Metairie, both of La.

[73] Assignee: The United States of America as represented by the Secretary of Agriculture, Washington, D.C.

[22] Filed: Dec. 5, 1974

[21] Appl. No.: 529,974

[44] Published under the second Trial Voluntary Protest Program on February 17, 1976 as document No. B 529,974.

Related U.S. Application Data

[62] Division of Ser. No. 376,971, July 6, 1973, Pat. No. 3,897,205.

[52] U.S. Cl. ............................. 260/568; 8/116 P; 252/8.8; 260/556 AR; 260/570.5 R
[51] Int. Cl.$^2$ ......................................... C07C 87/48
[58] Field of Search ...................... 260/568, 570.5 R

[56] References Cited
UNITED STATES PATENTS
3,897,205   7/1975   Frank et al. ........................... 8/116

OTHER PUBLICATIONS

Frank et al., "Journal Organic Chemistry," vol. 37, No. 17, pp. 2752–2755 (1972).

Primary Examiner—Robert V. Hines
Attorney, Agent, or Firm—M. Howard Silverstein; Salvador J. Cangemi; Max D. Hensley

[57] ABSTRACT

Novel quaternary arylaminoalkyl phosphonium salts having the formula [(ArNHCHR)$_4$P]$^+$X$^-$, where R is a radical selected from the group consisting of hydrogen, alkyl and aryl, Ar is aryl, and X is halogen, are prepared by the reaction of primary aromatic amines with quaternary hydroxyalkyl phosphonium salts having the formula [(HOCHR)$_4$P]$^+$X$^-$, where R and X are similarly defined. The compounds of this invention are useful as flame retardant for cotton, plasticizers, lubricant additives, and surface-active agents.

2 Claims, No Drawings

QUATERNARY ARYLAMINOALKYL PHOSPHONIUM SALTS

A non-exclusive, irrevocable, royalty-free license in the invention herein described, throughout the world for all purposes of the United States Government, with the power to grant sublicenses for such purposes, is hereby granted to the Government of the United States of America.

This is a division, of application Ser. No. 376,971, filed July 6, 1973, and now U.S. Pat. No. 3,897,205.

This invention relates to novel quaternary phosphonium salts. More particularly, it relates to quaternary phosphonium salts which contain four arylaminoalkyl substituents attached to each phosphorus atom.

The new quaternary arylaminoalkyl phosphonium salts have the general formula $[(ArNHCHR)_4P]^+X^-$ where R is a radical selected from the group consisting of hydrogen, alkyl and aryl, Ar is an aryl radical, and X is halogen.

In accordance with the practice of this invention, the new compounds are prepared by reacting a primary aromatic amine with a quaternary hydroxyalkyl phosphonium salt having the general formula $[(HOCHR)_4P]^+X^-$ where R and X are as defined above, in a molar ratio of at least 4:1, and separating the desired product from the reaction mixture.

It was reported in U.S. Pat. No. 3,035,053 that primary or secondary amines react with quaternary hydroxyalkyl phosphonium salts in a molar ratio of at least 4:1, giving rise to products that no longer contain the quaternary phosphonium salt structure, as shown in the following equation:

$4\ R_2NH + [(HOCHR)_4P]^+X^- \rightarrow (R_2NCHR)_3P + RCHO + R_2NH \cdot HX + 3\ H_2O$ One of the hydroxyalkyl substituents is seen to be removed in the form of the aldehyde, RCHO, and concomitantly the halogen, X, is removed in the form of the hydrogen halide salt of the primary or secondary amine. The phosphorus-containing product is seen to be a tertiary phosphine.

The primary or secondary amines that have been used for this purpose are usually strongly basic substances, such as diethylamine, cetylamine, morpholine, and the like, which are easily capable of removing hydrogen chloride from the quaternary hydroxyalkyl phosphonium salt, causing the rupture of the latter to a tertiary hydroxyalkyl phosphine and an aldehyde. This was demonstrated in U.S. Pat. No. 3,243,450 and in Zh. Obshch. Khim. 32, 553-57 (1962); Chem. Abstr. 58, 5714 h (1963) by causing the hydroxyalkyl phosphonium salt to react with a tertiary amine that is incapable of reacting further with the product, such as triethylamine. The resulting products are the tris(hydroxyalkyl)phosphine, the aldehyde, and the tertiary amine salt.

It is an object of the present invention to demonstrate that when the amine employed is a sufficiently weak base, such as a primary aromatic amine, this rupture does not occur, and it is possible to isolate the quaternary aminoalkyl phosphonium salt in good yield. This novel reaction can be illustrated as follows:

$4\ ArNH_2 + [(HOCHR)_4P]^+X^- \rightarrow [(ArNHCHR)_4P]^+X^-$

The primary aromatic amines which may be employed in the practice of this invention are characterized by the formula $ArNH_2$, where Ar is an aryl radical. Examples of these are aniline, o-toluidine, 2,4-xylidine, p-chloroaniline, m-nitroaniline, α-naphthylamine, β-naphthylamine, o-aminobiphenyl, benzidine, o-phenylenediamine, sulfanilamide, and the like.

The hydroxyalkyl phosphonium salts employed in the practice of this invention are characterized by the formula $[(HOCHR)_4P]^+X^-$, where R and X are as previously defined. These are exemplified by tetrakis(hydroxymethyl)phosphonium chloride (THPC), tetrakis(hydroxyethyl)phosphonium chloride, tetrakis(hydroxybenzyl)phosphonium chloride, and the like.

The reaction between the primary aromatic amine and the quaternary hydroxyalkyl phosphonium salt is most conveniently carried out simply by mixing the reactants together in the desired molar proportions in the presence of a solvent such as ethanol or acetone, and separating the product from the reaction mixture by filtration. The reaction can be carried out at temperatures ranging from 0° to 100°C., and at pressures either higher or lower than atmospheric pressure. If desired, the reaction may be performed in the absence of a solvent. The relative molar proportions of the reactants may be varied from 4:1 to 20:1, the preferred molar ratio being about 4:1 to 8:1. If the molar ratio is less than 4:1, as for example in Brit. Patent No. 761,985, the products are polymeric materials of indefinite structure.

The novel compounds of this invention are particularly useful as flame retardants for cotton, plasticizers, lubricant additives, and surface-active agents.

We have further found that the quaternary phosphonium salts of this invention are converted to two different kinds of tertiary phosphine upon treatment with strongly basic tertiary amines. In one kind, as exemplified by the reaction with triethylamine, the elements of the aldehyde, RCHO, are retained in the product, while in the other kind, exemplified by the reaction with ammonia, the aldehyde is released. These reactions may be illustrated as follows:

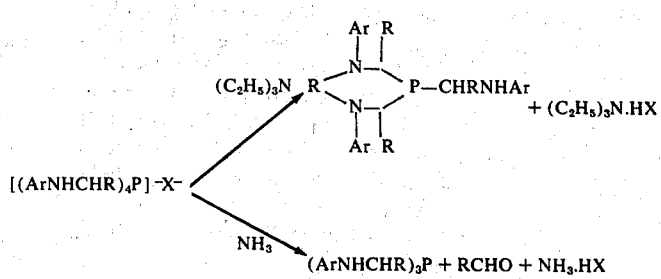

Both types of products exhibit the typical behavior of tertiary phosphines, forming derivatives such as the tertiary phosphine oxide and the tertiary phosphine sulfide, but the physical characteristics of the two kinds of tertiary phosphines and their derivatives are clearly different.

The following examples are presented to illustrate the novel compounds of this invention and their preparation, and are not to be construed as limiting the invention except as defined in the appended claims. All temperatures are in degrees centigrade and percentage are by weight.

Example 1

Aniline (7.70 g) was added to a solution of 3.83 g of tetrakis(hydroxymethyl)phosphonium chloride (THPC) in 75 ml of ethanol. There was a mild exotherm, followed immediately by the separation of solids. The mixture was stirred for 2 hours and then filtered, giving 9.15 g (93.0 percent yield) of tetrakis-(anilinomethyl)phosphonium chloride, m.p. 129°–130°, as a white crystalline solid that yellowed rapidly on exposure to light. No further solids separated from the filtrate in the next 5 hours. The filtrate and washings, stripped under vacuum, left 1.15 g of a yellow oil containing the remainder of the product and the unreacted aniline.

The product, which has the following structure,

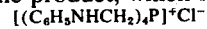
[($C_6H_5NHCH_2$)$_4$P]$^+$Cl$^-$ was analyzed and found to contain 68.18 percent carbon, 6.88 percent hydrogen, 11.33 percent nitrogen, and 6.33 percent phosphorus. The calculated percentages of these elements in $C_{28}H_{32}ClN_4P$ are 68.49 percent carbon, 6.57 percent hydrogen, 11.41 percent nitrogen and 6.31 percent phosphorus.

The infrared spectrum of the product, determined in a Nujol mull, showed a strong N-H absorption peak at 3290 cm$^{-1}$. The nuclear magnetic resonance spectrum, determined in dimethylsulfoxide-d$_6$, showed a multiplet in the 3.3 to 5.0 region assigned to CH$_2$, and another multiplet in the 6.3 to 7.3 δ region assigned to N-H and aromatic C-H. The ratio of the protons in the two multiplets was 8:24, in agreement with the assigned structure.

The product was insoluble in water and in the common organic solvents, but dissolved in highly polar solvents such as dimethylformamide or dimethylsulfoxide. It dissolved readily in hot chloroform or acetone, giving yellow solutions that deposited gums on workup, and in hot methanol or ethanol, giving disproportionation products.

EXAMPLE 2

Aniline (9.30 g) was added all at once to a slurry of 4.76 g of tetrakis(hydroxymethyl)phosphonium chloride (THPC) in 50 ml of acetone. The THPC dissolved within 1 minute, with slight warming, giving a clear solution that deposited solids on standing. After 2 hr, the mixture was filtered, giving 8.15 g (66.0 percent yield) of tetrakis(anilinomethyl)phosphonium chloride, m.p. 120°–121°. The filtrate, concentrated on a rotary evaporator, left 16.45 g of a neutral, dark yellow liquid. Beilstein tests on these products were strongly positive on the solid fraction and faintly positive on the liquid fraction, showing that most of the chlorine went into the solid fraction.

EXAMPLE 3

A piece of 3.2 oz. desized, scoured and bleached 80² cotton printcloth was padded through a solution of 15.0 g of tetrakis(hydroxymethyl)phosphonium chloride (THPC) and 0.2 g of a wetting agent in 34.8 g of water in a laboratory padder with a tight squeeze-roll setting (60 psi), two dips and two nips. The fabric was then dried for 4 minutes in a forced-draft oven at 85°, allowed to cool to room temperature, padded through a solution of 30.0 g of aniline in 20.0 g of ethanol, three dips and three nips, and then hung out on a clothesline to allow the reaction to proceed to completion and the fabric to air dry. The treated fabric was bright yellow in color, and the add-on was 44.6 percent.

A 1-cm strip of the treated fabric, ignited with a match at the lower end, passed the match test described by W. A. Reeves, O. J. Macmillan, and J. D. Guthrie, Textile Research Journal 23, 527 (1953) with a match test angle of 135°, showing the fabric to be flame retardant and self-extinguishing. When rinsed for 30 minutes in running tap water, the add-on dropped to 39.3 percent and the match test angle to 120°. The untreated cotton, by comparison, failed the match test even at 0°, and was completely consumed by the flames.

EXAMPLE 4

This example illustrates the conversion of a quaternary arylaminoalkyl phosphonium salt to a tertiary arylaminoalkyl phosphine without the loss of the aldehyde group.

Triethylamine (6.05 g) was added to a well-stirred slurry of tetrakis(anilinomethyl)phosphonium chloride (18.85 g) in 250 ml of acetone. There was no exotherm, but the appearance of the solid gradually changed to that of a much less voluminous, granular solid. After 1 hour, the solid was collected on a filter, washed with acetone, and dried, giving 4.45 g (84.0 percent yield) of triethylamine hydrochloride. No more separated on standing, nor upon the addition of more triethylamine to the filtrate. The filtrate was stripped of solvent under vacuum, and the residue, a yellow oil, was shaken vigorously with 250 ml of ethanol, whereupon it crystallized. After 2 hours, the solid was collected on a filter, washed with ethanol and dried, giving 10.50 g (76.0 percent yield) of 5-anilinomethyl-1,3-diphenyl-1,3,5-diazaphosphorinane as a white, crystalline solid, m.p. 96°–97°. The filtrate and washings yielded, upon evaporation, 7.40 g of a yellow oil from which 2.25 g (62.5 percent yield) of aniline was recovered by extracting with ether, drying over potassium hydroxide, and distilling.

The melting point, infrared spectrum and nuclear magnetic resonance spectrum of the 5-anilinomethyl-1,3-diphenyl-1,3,5-diazaphosphorinane thus prepared were identical to the melting point and spectra of the corresponding product prepared by neutralizing THPC with sodium ethoxide prior to reaction with aniline. This product, which had the following structure,

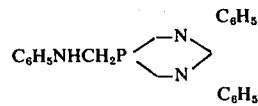

was analyzed and found to contain 73.36 percent carbon, 6.73 percent hydrogen, 11.48 percent nitrogen and 8.34 percent phosphorus; mol. wt. (osmometric, in CHCl$_3$), 359. The calculated percentages of these elements in $C_{22}H_{24}N_3P$ are 73.11 percent carbon, 6.69 percent hydrogen, 11.63 percent nitrogen and 8.57 percent phosphorus, mol. wt., 361.

The infrared spectrum of the product, determined in a Nujol mull, showed a weak but sharp N-H absorption peak at 3340 cm$^{-1}$. The nuclear magnetic resonance spectrum, determined in deutrochloroform, showed multiplets in the 3.2 to 4.0 δ region, assigned to PCH$_2$ and N-H groups; an ABX sextet centered at 4.23 and 5.06 δ, assigned to the NCH$_2$N group (representing the bound aldehyde group); and a multiplet in the 6.3 to 7.4 δ region, assigned to aromatic C-H. The ratio of the protons in the three multiplets was 7:2:15, in agreement with the assigned structure. The mass spectrum of the product showed the characteristic fragmentation pattern of methyleneaniline derivatives.

The product was soluble in chloroform, acetone and benzene, and insoluble in water and ether. It could be recrystallized from either cyclohexane or ethanol, but tended to oil out from both solvents unless seeded or scratched during cooling. Prolonged heating in ethanol, however, resulted in a hard transparent gum from which none of the product could be recovered.

In its reactions, the product showed the typical behavior of tertiary phosphines, giving as crystalline derivatives the tertiary phosphine oxide, m.p. 170°–171°, and the tertiary phosphine sulfide, m.p. 127°–128°.

EXAMPLE 5

This example illustrates the conversion of a quaternary arylaminoalkyl phosphonium salt to a tertiary arylaminoalkyl phosphine concomitant with the loss of the aldehyde group.

Ammonia was bubbled into a slurry of tetrakis-(anilinomethyl)-phosphonium chloride (4.90 g) in 50 ml of acetone for 5 minutes at room temperature, during which time the solid dissolved and was replaced by a finely divided white precipitate. After 30 minutes, the mixture was filtered, giving 0.50 g (93.5 percent yield) of ammonium chloride. The filtrate was stripped of solvent under vacuum, and the residue (5.60 g), which contained no chlorine as determined by a Beilstein test, was shaken vigorously with 250 ml of ethanol, whereupon it crystallized. The solid was collected on a filter, washed with ethanol and dried, giving 2.40 g (61.9 percent yield) of tris(anilinomethyl)phosphine as a white, crystalline solid, m.p. 87°–88°. The filtrate and washings yielded, upon evaporation, 2.60 g of a pale yellow oil from which 0.90 g (96.8 percent yield) of aniline was recovered by extracting with ether, drying over potassium hydroxide, and distilling.

The melting point, infrared spectrum and nuclear magnetic resonance spectrum of the tris(anilinomethyl)phosphine thus prepared were identical to the melting point and spectra of the corresponding products obtained by the reaction of aniline with tris(hydroxymethyl)phosphine or tris(dimethylaminomethyl)phosphine, neither of which contained the potential aldehyde group.

The product, which had the following structure, (C$_6$H$_5$NHCH$_2$)$_3$P was analyzed and found to contain 73.81 percent carbon, 7.17 percent hydrogen, 10.73 percent nitrogen and 7.79 percent phosphorus. The calculated percentages of these elements in C$_{24}$H$_{27}$N$_3$P is 74.02 percent carbon, 7.01 percent hydrogen, 10.82 percent nitrogen and 7.97 percent phosphorus.

The infrared spectrum of the product, determined in a Nujol mull, showed an N-H absorption peak at 3440 cm$^{-1}$ that was much stronger than the corresponding peak in the product of Example 4, reflecting the presence of three N-H groups instead of one. The nuclear magnetic resonance spectrum, determined in deuterochloroform, showed none of the fine structure of the product of Example 4, with a doublet at 3.52 assigned to CH$_2$, a singlet at 3.64δ assigned to N-H, a multiplet in the 6.6 to 7.2 δ region assigned to aromatic C-H, and a singlet at 7.37 δ assigned to solvate benzene. The ratio of the protons in the four groups of peaks was 6:3:15:3, in agreement with the assigned structure.

The product retained the solvate benzene tenaciously. A sample dried in a drying pistol under vacuum at 80°, however, lost 37.2 percent of its weight and was no longer crystalline.

The product was insoluble in water on ether, but dissolved instantly in acetone or chloroform. In its reactions it showed the typical behavior of tertiary phosphines, giving as crystalline derivatives the tertiary phosphine oxide, m.p. 122°–123°, and the tertiary phosphine sulfide, m.p. 105°–106°. These derivatives, like the product itself, were clearly different from those of Example 4.

The foregoing description is given for clearness of understanding only, and is not intended to limit the scope of the invention in any way, as modifications will be obvious to those skilled in the art.

We claim:

1. A quaternary arylaminoalkyl phosphonium salt having the formula (ArNHCH$_2$)$_4$P$^+$Cl$^-$ where Ar is radical selected from the group consisting of phenyl, tolyl, xylyl, chlorophenyl, nitrophenyl, and naphthyl.

2. Tetrakis(anilinomethyl)phosphonium chloride.

* * * * *